US006515022B2

(12) United States Patent
Tong et al.

(10) Patent No.: US 6,515,022 B2
(45) Date of Patent: Feb. 4, 2003

(54) USE OF INHALED RETINOIDS IN THE TREATMENT OF LUNG DISEASES

(75) Inventors: William P. Tong, Flushing, NY (US); Raymond P. Warrell, Jr., Westfield, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/854,331

(22) Filed: May 11, 2001

(65) Prior Publication Data

US 2002/0035152 A1 Mar. 21, 2002

Related U.S. Application Data

(63) Continuation-in-part of application No. 09/171,478, filed as application No. PCT/US97/05409 on Apr. 21, 1997, now Pat. No. 6,251,941.
(60) Provisional application No. 60/016,246, filed on Apr. 19, 1996.

(51) Int. Cl.$^7$ ................................................ A61K 31/20
(52) U.S. Cl. ...................................... 514/559; 514/558
(58) Field of Search ......................................... 514/559

(56) References Cited

U.S. PATENT DOCUMENTS 4,529,600 A    7/1985   Dawson et al. ............. 514/529

OTHER PUBLICATIONS

F. Moren et al., "Aerosols in Medicine—Principles, Diagnosis and Therapy", (1993) eds.. Elsvier, New York, New York, 1993.

Molecusol brochure (1988).

Hong et al., "Prevention of Second Primary Tumors with Isoretinoin in Squamous–Cell Carcinoma of the Head and Neck" New Engl. J. Med. 323: 795–801 (1990).

Laznitzki et al., "Prevention and Reversal by a Retinoid of 3,4–Beanzpyrine– and Cigarette Smoke Condensate–Induced Hyperplasia and Metaplasia of Rodent Respiratory Epithella in Organ Culture", Cancer Treatment Rep. 66: 1375–1380 (1982).

Warrell, Jr. R.P., "Retinoids in Cancer", in *ImmunoPharmaceuticals*, E.S. Kimball, ed., CRC Press, New York, New York, (1993), pp. 101–128.

Osol et al., Editor of *Remington's Pharmaceutical Sciences*, 15$^{th}$ Edition, (1975), p. 1651.

Windholz et al., Editor of *The Merk Index*, 10$^{th}$ Edition, p. 1381, (1983).

Stein et al., Editor of *Internal Medicine*, 4$^{th}$ *Edition*, Chapters 71–72, pp. 699–715, (1993).

*Primary Examiner*—Dwayne C. Jones
(74) *Attorney, Agent, or Firm*—Oppedahl & Larson LLP

(57) ABSTRACT

Administration of retinoids by inhalation is used to overcome the chronic toxicity problems presented by systemic administration and to make retinoid therapy available as an option for the treatment of fibrotic lung disease, emphysema, and the prevention and treatment of epithelial cancers of the respiratory tract, especially those that are associated with tobacco use. Retinoids are administered by inhalation to the respiratory tract of the individual as an air-borne composition with a metered dose aerosol-producing inhaler, in which the retinoid is dissolved in a combination of a pharmaceutically acceptable chlorofluorocarbon propellant and an alkylamine solubilizing agent.

21 Claims, 3 Drawing Sheets

ALL-TRANS RETINOL

14-HYDROXY-RETRO-RETINOL

ALL-TRANS RETINOIC ACID

N-(4-HYDROXYPHENYL) RETINAMIDE

13-CIS RETINOIC ACID

3-METHYL TTNEB

9-CIS RETINOIC ACID

MEAN PLASMA LEVELS OF ATRA
(n=3-5 TIME POINT [TP]), IV (n=5/TP), OR INTRA-TRACHEAL
INJECTION (n=3/TP).

MEAN LIVER LEVELS OF ATRA
(n=3-5/TIME POINT[TP]), IV (n=5/TP), OR INTRA-TRACHEAL
INJECTION (n=3/TP).

LOG OF MEAN LUNG LEVEL OF ATRA
(n=3-5/TIME POINT [TP]), IV (n=5/TP), OR INTRA-TRACHEAL
INJECTION (n=3/TP). THERE IS NO DATA FOR THE INTRA-
TRACHEAL OR IV DOSED ANIMALS AT 24 HRS.

USE OF INHALED RETINOIDS IN THE TREATMENT OF LUNG DISEASES

This application is a continuation-in-part of U.S. patent application Ser. No. 09/171,478 filed Dec. 29, 1998, now U.S. Pat. No. 6,251,941, which is a national phase of International Application Ser. No. PCT/US97/05409 filed Apr. 21, 1997 which claims the benefit of priority from U.S. Provisional App. Ser. No. 60/016,246 filed Apr. 19, 1996.

BACKGROUND OF THE INVENTION

Retinoids are a class of naturally occurring and synthetic derivatives of vitamin A which function in vivo as regulators of a number of physiological functions including cellular proliferation, cytodifferentiation and embryonal morphogenesis. In rodents, vitamin A deficiency induces epithelial dysplasia in the tracheobronchial tree, whereas in humans, exogenous treatment with retinoids induces terminal differentiation of certain premalignant lesions of the skin, oral mucosa, and uterine cervix. Meyskens, et al, JNCI 86:539 (1994). The class of retinoids includes a number of clinically important compounds such as those shown FIG. 1 which have been shown or hypothesized to have utility in the therapy and prevention of various types of cancer. For example, Hong et al., N. Eng. J. Med. 323: 795–801 (1990) have shown that adjuvant treatment with 13-cis retinoic acid after definitive anti-cancer treatment in patients with carcinoma of the head and neck significantly reduces the incidence of secondary tumors of the aerodigestive tract. Head and neck cancer, like lung cancer, is significantly related to tobacco smoking, and in fact many of the tumors reduced in incidence in the Hong et al. study were lung cancers. Retinoids have produced striking therapeutic results in patients with acute promyelocytic leukemia, doubling the proportion of patients cured of this highly lethal disease. Warrell, et al., NEJM 329:177 (1993) and Soignet et al., Cancer Chemother. Pharmacol. 40 (Suppl.):S25–S29 (1997). Retinoids have also been shown to be effective in the prevention and reversal of certain types of induced hyperplasia and metaplasia in cultured rodent respiratory epithelial. Lasnitzki et al., Cancer Treatment Reports 66: 1375–1380 (1982). Evidence also suggests that all-trans retinoic acid may induce the proliferation of alveolar cells in lungs that have been damaged by fibrosis. Massaro, et al., Nature Med 3:675 (1997). This surprising observation has suggested that retinoids may have important utility for the treatment of patients with pulmonary emphysema. Chemoprevention trials with retinoids have so far been confined to orally administered drugs, which expose the drug to first-pass metabolism in the liver. Moreover, continuous daily treatment with all-trans retinoic acid is associated with a progressive reduction in plasma drug levels, which may further reduce clinical efficacy.

Unfortunately, while retinoids have been shown to provide beneficial effects in the prevention of at least some types of cancer, the therapeutic regiment requires chronic administration. Under these circumstances, substantial systemic toxicity may result, including hepatic dysfunction, skeletal malformations, mucositis, hyperlipidemia, hypertriglyceridemia (possibly leading to accelerated atherosclerosis and pancreatitis), hypercalcemia, birth defects, and skin, liver and central nervous system toxicity. This toxicity has limited the utility of retinoids as therapeutic agents in the prevention of cancer and in the treatment of lung diseases.

Several potential strategies for mitigating the toxicity of retinoids have been considered, including "drug holidays", reductions in dosage, and development of naturally occurring or synthetic ligands that bind specific nuclear retinoid receptors. Lotan, R., FASEB J 10: 1031 (1996). However, none of these strategies has yielded a substantial increase in therapeutic index.

For many drugs, organ-specific targeting, including the inhaled route, has been an effective means of drug delivery. In addition to significantly increasing local drug concentrations at the desired site, this route avoids the "first pass" effect that occurs with transport through the liver. Inhalation therapy has proved especially useful for the treatment of lung diseases including asthma, cystic fibrosis, and P. carinii prophylaxis. J Allergy Clin Immun 88(3):451 (1991).

The ability to provide retinoid therapy for extended periods of time without the systemic toxic effects would enable treatment and prevention of various lung diseases including cancer and emphysema.

SUMMARY OF THE INVENTION

We have developed a system for administration of retinoids by inhalation to overcome the chronic toxicity problems presented by systemic administration, to increase the local bioavailability of the retinoids and to make retinoid therapy available as an option for the prevention of epithelial cancers and diseases of the respiratory tract, especially those that are associated with tobacco use. Thus, in accordance with the present invention, there is provided a method for treating lung diseases and preventing epithelial cancer of the respiratory tract in an at-risk individual, comprising administering by inhalation to the respiratory tract of the individual an air-borne composition (i.e., an aerosol or finely divided dry powder) comprising a therapeutically effective amount of at least one retinoid. The retinoid is suitably administered with a metered dose aerosol-producing inhaler, in which the retinoid is dissolved in a combination of a pharmaceutically acceptable chlorofluorocarbon propellant and an amine solubilizing agent.

DETAILED DESCRIPTION OF THE INVENTION

Figure 1:
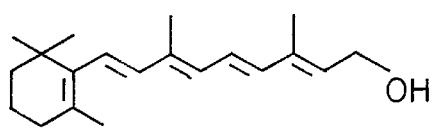
FIG. 1 shows the structures of various clinically significant retinoids.
Figure 1:
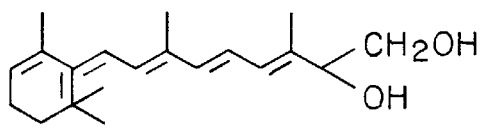
Figure 1:
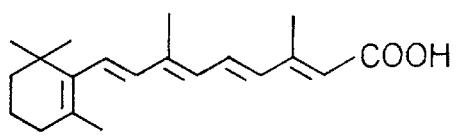
Figure 1:
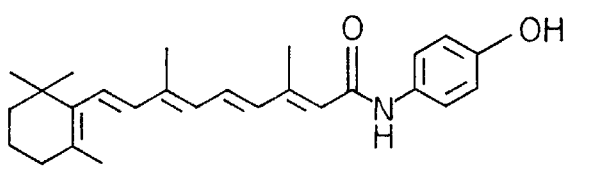
Figure 1:
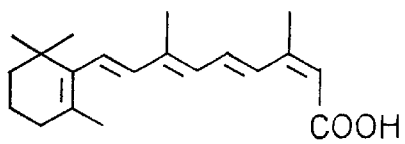
Figure 1:
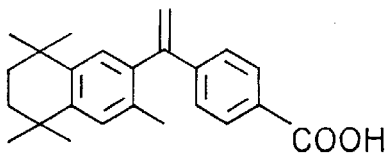
Figure 1:
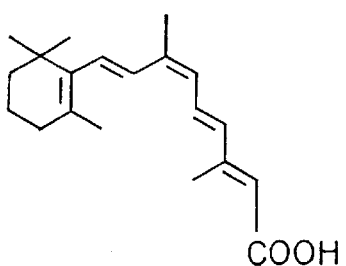

The present invention relates to the treatment of lung diseases and prevention of epithelial cancer of the respiratory tract in an at-risk individual by administering by inhalation to the respiratory tract of the individual an aerosol comprising a therapeutically effective amount of at least one retinoid. The method provides delivery of the pharmaceutically active retinoid directly to the affected areas, thus increasing bioavailability and decreasing systemic toxicity. It will be recognized by persons skilled in the art that "prevention" of cancer is difficult to prove in the absolute sense because one cannot predict with certitude what will transpire in the future. Thus, as used in the specification and claims of this application, the terms "prevention" or "preventing" refer to a reduction of the risk of contracting epithelial cancer, or to a delay in the onset of epithelial cancer.

Inhalation of pharmaceutically-active compositions is not a new concept, and various compounds used in asthma therapy and the like have been administered in this manner. The major advantage is site-specific drug delivery which often leads to reduced systemic drug levels. The avoidance of elevated serum and liver drug levels should enable long term therapy for cancer chemoprevention in high risk individuals, as well as persons with fibrotic lung disease. Commonly, however, aerosols are formed from the active compounds solubilized in water. However, most retinoids of clinical interest, including all of the "natural retinoids" such as all-trans retinoic acid, 13-cis retinoic acid and 9-cis retinoic acid, are highly lipophilic and thus very insoluble in water. For this reason, conventional water-based formulations cannot be used for aerosol administration of these compounds. To make it possible to perform inhalation therapy using retinoids, it was therefore necessary to define a solvent system which (1) solubilized sufficient amounts of the retinoids to provide a pharmaceutically-useful dosage, i.e., from about 0.1 to 5.0 mg/ml; (2) provided a retinoid solution of sufficient stability to permit distribution of a product; and (3) was substantially non-toxic in the amounts administered and thus suitable for administration to living patients.

Working towards this goal, we first looked at organic solvents. In the course of this investigation, we found that retinoids were only slightly soluble in ethanol or ethyl acetate. Methylene chloride or chloroform provided adequate solubilization, but the potential toxicity of these materials argued against their use as carriers in an aerosol for use in inhalation therapy.

Next, because of a report that the solubility of retinol (vitamin A) in water could be increased by addition of modified beta cyclodextrin (MOLECUSOL®), we next tried to prepare aqueous solutions of all-trans retinoic acid using MOLECUSOL® to enhance the solubility. Solutions containing 45% MOLECUSOL® did in fact enhance the solubility of the all-trans retinoic acid to a useful level, but the resulting solution had a thick, syrupy consistency which was unsuited for use in the generation of an aerosol. Similarly, efforts to solubilize all-trans retinoic acid in aqueous solution using phosphatidylcholine and phosphatidylethanolamine produced a viscous colloid which was unsuited for aerosol administration.

We next tried to use salts of the retinoids to obtain a water-soluble product for aerosol generation. When all-trans retinoic acid is treated with ammonium hydroxide, a water-soluble ammonium salt is obtained. The pH of solutions of this salt is too high (pH >10), however, for direct administration as an aerosol. Neutralization of the solution after dissolution of the retinoid led to the formation of a precipitate, both in the presence and absence of added beta cyclodextrin. Thus, this approach also failed to produce an acceptable solution for use in generating an aerosol.

Because of the solubility of all-trans retinoic acid in halogenated hydrocarbon solvents, we next considered the solubility of retinoids in various chlorofluorocarbon propellants which have been used to deliver aerosolized solutions of other pharmaceutically-active compounds. All-trans retinoic acid was found to be only slightly soluble (about 0.1 mg/ml) in 1,1,2-trichlorofluoroethane and only slightly more soluble (2 mg/ml) in 2,2-dichloro-1,1,1-trifluoroethane (HCFC-123). Thus, as an initial matter, it did not appear that these solvents would be useful for producing solutions of retinoids for inhalation use.

Surprisingly, however, we found that the solubility of retinoids in chlorofluorocarbon solvents could be significantly increased by the addition of alkylamines, particularly secondary, tertiary and quaternary alkylamines having alkyl groups containing from 2 to 8 carbon atoms such as trioctylamine, spermine, triethylamine or tetramethylammonium bromide, and that the resulting solutions were stable for periods of 5 days or longer, and could be solubilized by shaking. Thus, one aspect of the present invention is a solution comprising a retinoid, a chlorofluorocarbon solvent, for example HCFC-123, HCFC-134A or HCFC-227, and an alkylamine which is effective to solubilize the retinoid in the chlorofluorocarbon solvent. The solution preferably contains from 0.1 to 10 mg of the retinoid and 0.1 to 5 mg of the alkylamine, more preferably 1 to 2 mg of the retinoid and 0.1 to 0.5 mg of the alkylamine, per ml of solution.

Retinoids useful in the present invention include the "natural retinoids" as well as pharmaceutically acceptable salts and esters thereof. Retinoids of particular interest in the present invention are all-trans retinoic acid, 13-cis retinoic acid, 9-cis retinoic acid, and salts and esters thereof.

The alkylamine is suitably a charged or uncharged secondary, tertiary or quaternary amine, having alkyl groups of 2 to 8 carbon atoms. Specific examples of suitable alkylamines include trioctylaimie, triethylamine, spermine and tetrabutylanmonium bromide.

Figure 2:
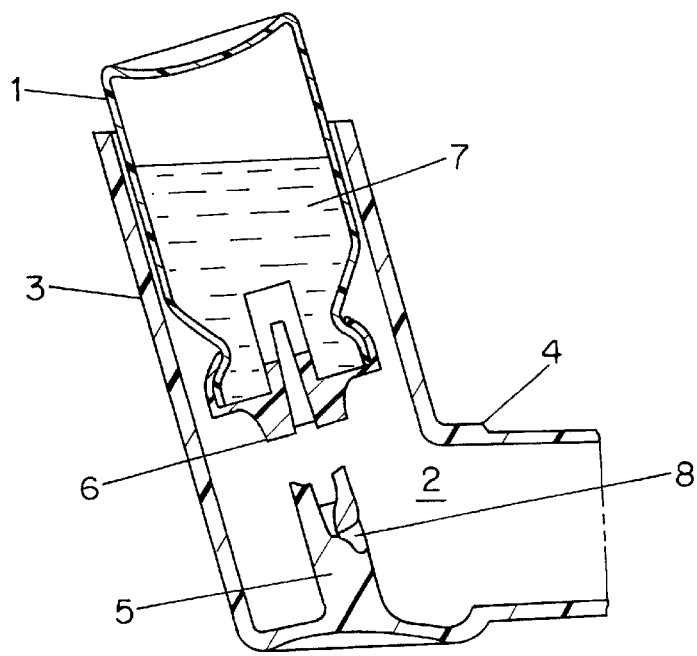
FIG. 2 shows an inhaler in accordance with the invention.

This solution is packaged in an inhaler effective to provide a metered dosage of from 50 to 500 $\mu$g, preferably about 100 $\mu$g, of retinoid per inhalation as shown generally in FIG. 2. Such an inhaler is a combination of a container 1 and a dispenser assembly 2. The dispenser assembly 2 is an open tubular construction which has an actuator portion 3 for receiving the container 1, an oral tube 4 through which the retinoid is dispensed, and an actuator seat 5 which interacts with a metering valve 6 of the container 1. When the container 1 is pressed downwards within the actuator portion 3, the actuator seat 5 opens the metering valve 6, releasing a dose of retinoid 7 from the container 1, through an orifice 8 in the actuator seat 5 and out through the oral tube 4. A suitable inhaler is a Nasacort® metered dose container. Additional propellant material, for example butane, may be included within the inhaler.

The inhaler is used to administer retinoids directly to the lungs of a patient at risk of epithelial cancer of the respiratory tract. Patients in this category can be identified by behavioral characteristics. For example, individuals who are heavy smokers can be categorized as being at high-risk. Alternatively, a more quantitative approach may be used. Thus, the capacity to metabolize a small test dose of all-trans retinoic acid can be used as an indicator of risk, as described in U.S. patent application No. 07/885,130 filed May 18, 1992, which is incorporated herein by reference.

The inhaler provides dosages of from 50 to 500 $\mu$g of retinoid per inhalation and is suitably used 1 to 5 times per treatment, with the treatment being repeated 1 to 3 times per day.

A further format which can be used in accordance with the invention to administer an air-borne composition comprising a retinoid to an individual involves the use of a dry powder carrier. Suitable carriers include those which are known to be useful in dry powder inhaler compositions especially the mono-saccharides such as fructose, manintol, arabinose, xylitol and dextrose (glucose) and their monohydrates, disaccharides such as lactose maltose or sucrose and polysaccharides such as starches, dextrins or dextrans. Retinoids can be formulated into a dry powder with these carrier materials by coating the retinoid onto the surface of the carrier in a micronizer as described generally in U.S. Pat. No. 5,376,386 which is incorporated herein by reference. Dry powders containing retinoids are dispensed using known dry powder inhalers in amounts effective to provide dosages comparable to the solubilized formulations discussed above.

EXAMPLE 1

The solubility of all-trans retinoic acid in various solvents was tested as shown in Table 1. Maximum solubility was determined by weighing the residue remaining after evaporation of the solvent.

TABLE 1

| Solvent | Maximum Solubility |
|---|---|
| ethyl acetate | 10 mg/ml |
| methylene chloride | 5 mg/ml |
| HCFC-123 | ~2 mg/ml |

EXAMPLE 2

To test the ability of alkylamines to enhance the solubility of all-trans retinoic acid in chlorofluorocarbons, solutions of the retinoids in various solvents with various amounts of amine stabilizers were prepared as shown in Table 2.

TABLE 2

| Solvent | AlkylAmine- (mg/ml) | Maximum Solubility (mg/ml) |
|---|---|---|
| HCFC-123 | 0 | ~2 |
| HCFC-123 | 1.44 | ~17 |
| HCFC-123 | 7.22 | ~44 |

EXAMPLE 3

To evaluate the bioavailability of retinoids delivered by inhalation, 100 μl of an aqueous solution containing 100 μg of all-trans retinoic acid was administered via intra-tracheal instillation to 3 Sprague-Dawley rats, each weighing approximately 200 g. One rat was then sacrificed at three time points: 1, 6 and 24 hours after treatment. At the time of sacrifice, the chest cavity was opened, both lungs and trachea were removed en bloc, and the right and left lungs were separated by dissection. The liver was also removed, along with a sample of blood obtained by cardiac puncture. The blood sample was separated by centrifugation, and plasma plus each of the aforementioned tissues were frozen for later analysis. Subsequently, the tissue was homogenized, and the homogenized tissue and plasma were extracted with ethanol. The retinoid content was assayed by HPLC, and the results shown in Table 3 were obtained.

TABLE 3

Tissue/Plasma Concentrations of Retinoic Acid After Intra-Tracheal Instillation (ng/g or tissue or ng/ml of plasma)

| Hours | Trachea | Left Lung | Right Lung | Plasma | Liver |
|---|---|---|---|---|---|
| 1 | 2859 | 928 | 773 | 123 | 233 |
| 6 | 96 | 56 | 91 | ND | 24 |
| 24 | 30 | 22 | 21 | 178 | 23 |

The results show that this approach provides high levels of retinoid locally, but does not lead to high systemic levels.

EXAMPLE 4

The biodistribution and pharmacokinetics of an inhaled formulation of all-trans retinoic acid were compared to both intra-tracheal and intravenous administration. Anesthetized (i.p. pentobarbitol 50 mg/kg) male Sprague-Dawley rats weighing 300 to 700 grams were treated by administration of all-trans retinoic acid by inhalation, iv injection or intra-tracheal injection. Inhaled and intra-tracheal injections were given through an endotracheal tube placed under direct vision over a guidewire as described by Weksler et al., *J. Appl. Physiol.* 76: 1823–1825 (1994). IV doses were given by catheter injection via the right external jugular vein.

For inhalation, all-trans retinoic acid was solublized in hydrofluorocarbon 123 using tetramethylamunonium hydroxide to a concentration of 5 mg/ml, and combined with hydrofluoroalkane 134a as propellant, for a final concentration of 1.5 mg per 1.475 grams of propellant solution. 21 grams of this solutions was packaged in a multidose inhaler that delivered 77.5 mg of product per dose, which resulted in 80 to 120 mg of all-trans retinoic acid per dose. An identical inhaler containing propellant mixture without drug was used as a control. When sprayed through the endotracheal tube, the test canister supplied 49 μg/dose. However, not all of this dose was absorbed by the rats due to escape through the nasal passages and back through the trachea. The actual amount of drug delivered to the lungs (defined as the "effective dose") was calculated by delivering 10 doses through the aerosol delivery apparatus into a flask that contained 100 ml of isopropanol. This procedure was also repeated with an angiocatheter fitted to the apparatus. The catheter was subsequently rinsed with 10 ml of isopropanol, which was also collected. The three solutions were then assayed for all-trans retinoic acid concentrations in order to determine the amount of drug delivered through the apparatus, as well as any residual drug that was bound to the angiocatheter. We defined the area under the concentration times-time curve (AUC) for animals who received intra-tracheal all-trans retinoic acid as 100% effective dose delivery to the lung. The AUC of the inhaled aerosolized drug was divided by the intra-tracheal AUC in order to determine the percent effective dose. Total absorption amounted to 1–2% of the intended 250 μg dose.

For injection, an aqueous solution of all-trans retinoic acid was prepared in 20% ethanol, 10% Tween 20 and 1 mM $NH_4OH$, for a final concentration of 1 ml all-trans retinoic acid per ml of solution. A mixture of 20% ethanol and 10% Tween 20 served as a control.

Animals were grouped into three experimental groups and two control groups. The control groups received no treatment or a control inhalant containing no all-trans retinoic acid. Animals in the groups receiving iv or intra-tracheal injections each received a single dose containing 250 μg all-trans retinoic acid. Animals in the group treated with the multidose inhaler each received three doses for a total of 147 μg of all-trans retinoic acid.

Animals were sacrificed at 5 minutes and at 1, 2, 4 and 6 hours, and blood and liver and lung tissue were harvested for analysis by high performance liquid chromatography (HPLC) and histology. In addition, animals receiving the inhalant were sacrificed at 24 hours post-treatment.

Figure 3A:
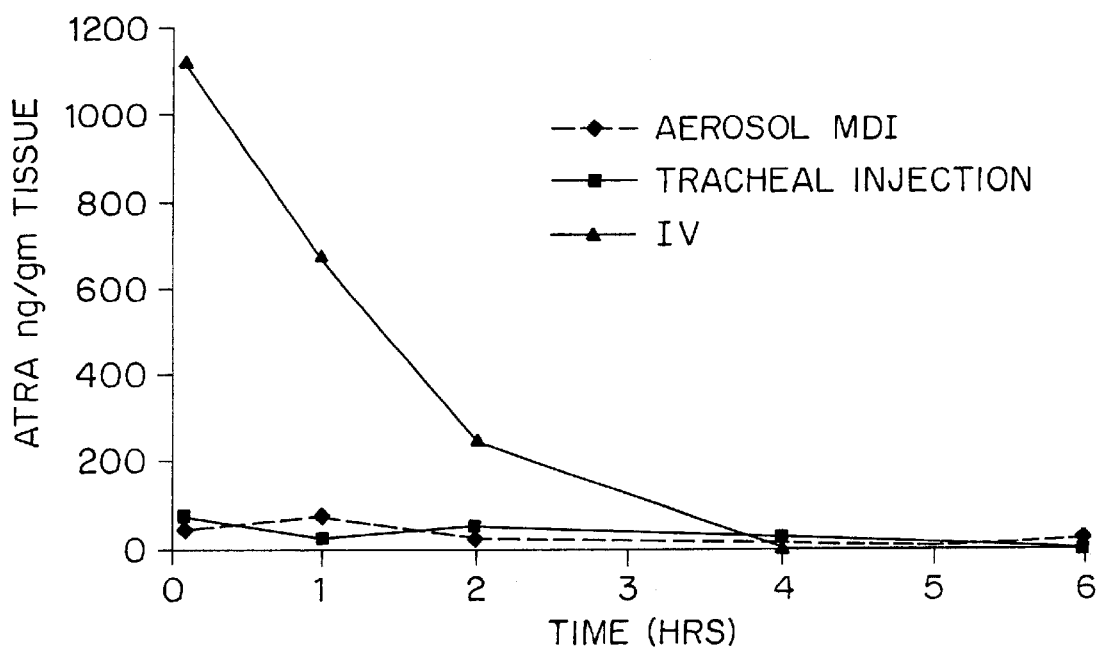
FIGS. 3A and 3B show plasma and liver levels, respectively, of all-trans retinoic acid after administration to rats using three different routes.
Figure 3B:
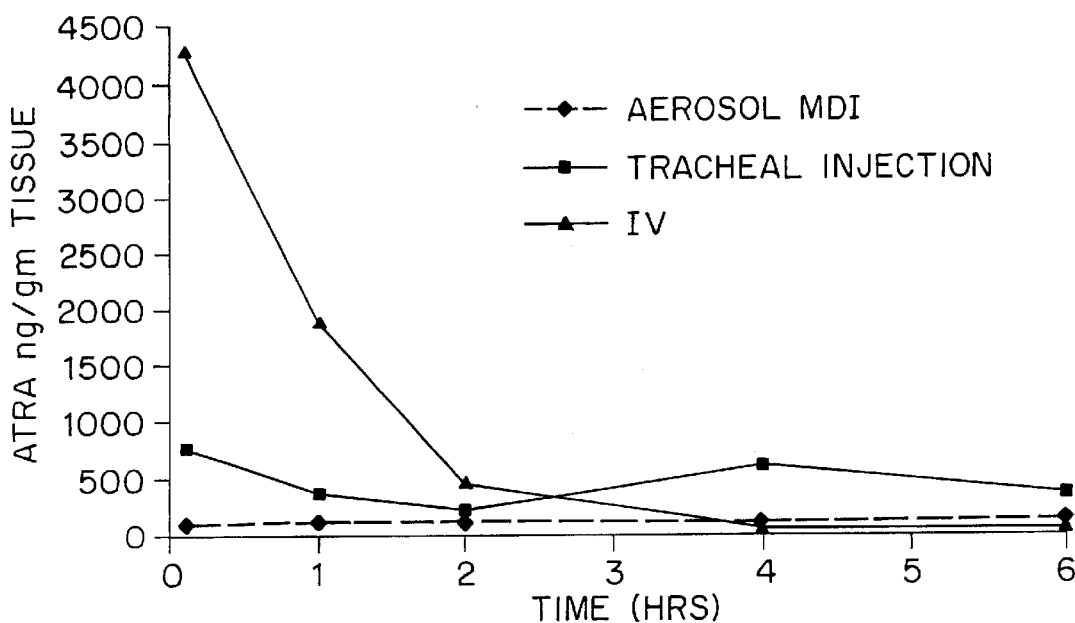
Figure 4:
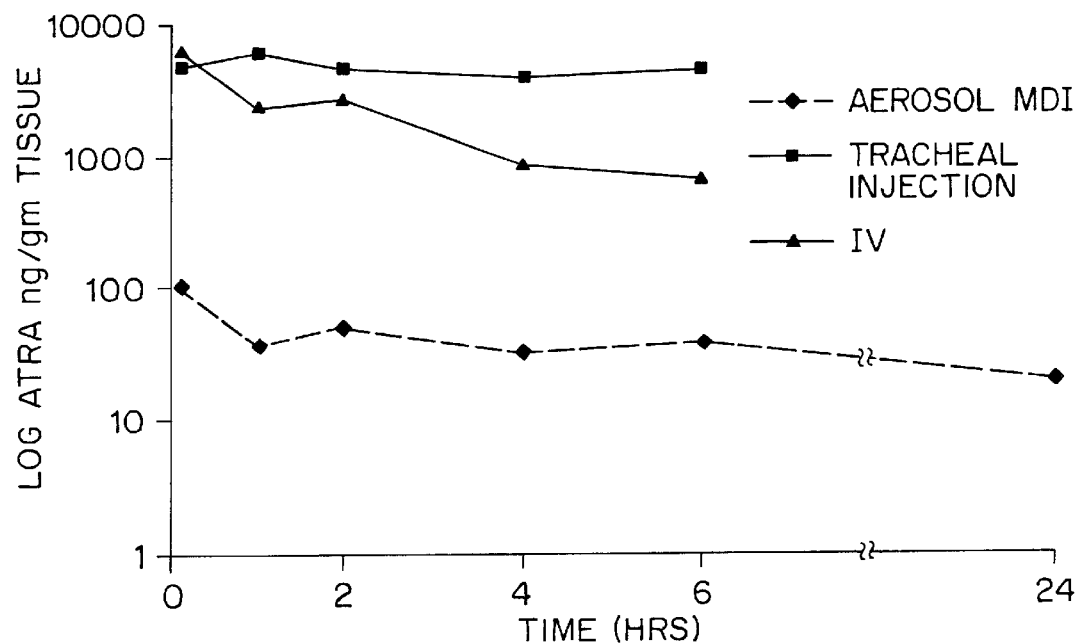
FIG. 4 shows lung tissue levels of all-trans retinoic acid after administration to rats using three different routes.

FIGS. 3A and 3B show the levels of all-trans retinoic acid found in the plasma and livers of animals in each of the three treatment groups. As shown, intra-tracheal injection and aerosol inhalation result in much lower levels of the compound in the liver (FIG. 3B). On the other hand, as shown in FIG. 4, all three treatments resulted in prolonged levels of all-trans retinoic acid in the lungs where it is desired for therapeutic efficacy. Clearance data from plasma and lung and liver tissue is summarized in Table 4.

TABLE 4

| Admin. Route | Lung T½ (hours) | Lung AUC (ng-hr/gm) | Plasma T½ (hours) | Plasma AUC (ng-hr/ml) | Liver T½ (hours) | Liver AUC (ng-hr/gm) |
|---|---|---|---|---|---|---|
| iv inj. | 1.9 | 11910 | 0.9 | 1385 | 0.8 | 4724 |
| intra-tracheal inj. | 17.7 | 26972 | 1.9 | 191 | 22 | 2532 |
| aerosol inhaler | 5.4 | 262 | 3 | 171 | —[a] | 2307 |

[a]unable to calculate T½ without decay curve.

In animals who received the metered dose inhaler, lung concentrations of all-trans retinoic acid were highest at 5 minutes (99±44 ng/gm of tissue), followed by a slow decrease over the next 24 hours (FIG. 4). The calculated tissue half-life of the aerosolized drug in lung was 5.4 hours. Animals who received intra-tracheal injections showed peak lung levels at 1 hour (5,767±419 ng/gm), which were maintained for approximately 6 hours. The lung tissue half-life ($T_{1/2}$) was 17.7 hours by the intra-tracheal route. Peak lung levels by the iv route were seen at 5 minutes (6,440±1,865 ng/gm) and disappeared with a half-life of 1.9 hours. The lung levels by the inhaled route were significantly lower than the intra-tracheal route at each time point ($p<0.02$); however, the difference from the iv route was only significant before the 2 hour post dosing time point. The lung AUC, an indication of total drug delivery to an organ over time, for the intra-tracheal route was twice that of the iv route and 100 times that of the aerosolized route (Table 4).

Animals receiving aerosolized drug displayed peak plasma levels of 71±31 ng/ml 1 hour after dosing, which was not significantly different from intra-tracheal administration at 1 hour (68±44 ng/ml) (FIG. 3A). By contrast, animals in the iv group displayed a characteristic plasma curve with a peak at 5 minutes (838±56 ng/ml) and a rapid decay ($T_{1/2}=$ 0.4 hours). Differences between the iv and the other groups were significant up to 4 hours ($p<0.05$).

Animals in the inhaled drug group had peak liver levels of 112±28 ng/gm 2 hours after dosing, whereas intra-tracheal injection produced peak liver levels of 753±350 ng/gm at 5 minutes (FIG. 3B). Both groups showed a slow decrease over 24 hours. In contrast, iv administration resulted in peak levels in liver at 5 minutes (4,258±1,006 ng/gm), which had rapidly decreased by 4 hours ($T_{1/2}=1$ hour).

Compared with iv injection, aerosolization and intra-tracheal injection of all-trans retinoic acid resulted in a significantly longer pulmonary half-life of the drug and lower peak serum concentrations than the same dose administered iv. As shown, the aerosol inhalation provided sustained levels of all-trans retinoic acid in the lungs with lower levels in the plasma compared to iv injections, thus offering the ability to use all-trans retinoic acid as a therapeutic agent with a reduction in systemic toxicity. Histologic examination of lungs and traches showed no focal irritation attributable to the drug after single-dose administration. These results suggest that aerosolization of retinoids may offer a practical alternative to systemic oral administration for chemoprevention trials or treatment of lung diseases.

The advantages of inhaled drug delivery are well-characterized. Site-specific drug delivery is readily accomplished, and the portability of multi-dose inhalers, their ease of use, and reduced adverse effects should improve patient compliance. Moreover, the avoidance of elevated serum and liver drug levels should further enable long term therapy for cancer chemoprevention in high risk (by asymptomatic) persons, as well as individuals with fibrotic lung disease.

Although the preferred embodiment of the method and products of the invention has been described above in some detail, it should be appreciated that a variety of embodiments will be readily apparent to one skilled in the art. The description of the method and products of this invention is not intended to be limiting to this invention, but is merely illustrative of the preferred embodiment.

We claim:

1. A method for the treatment of lung disease in the respiratory tract in an individual, comprising administering by inhalation to the respiratory tract of the individual an air-borne composition comprising a therapeutically effective amount of at least one retinoid.

2. The method of claim 1, wherein the retinoid is administered in a solution comprising a retinoid, a chlorofluorocarbon solvent, and an amine which is effective to solubilize the retinoid in the chlorofluorocarbon solvent.

3. The method of claim 2, wherein the solution comprises from 0.1 to 10 mg of the retinoid and from 0.1 to 5 mg of the alkylamine per ml of solution.

4. The method of claim 3, wherein the solution comprises from 1 to 2 mg of the retinoid and 0.1 to 0.5 mg of the alkylamine per ml of solution.

5. The method of claim 2, wherein the retinoid is all-trans retinoic acid.

6. The method of claim 2, wherein the alkylamine is a secondary, tertiary or quaternary alkylamine having alkyl groups containing from 2 to 8 carbon atoms.

7. The method of claim 2, wherein the alkylamine is selected from the group consisting of trioctylamine, triethylamine, spermine and tetrabutylammonium bromide.

8. The method of claim 1, wherein the lung disease is a fibrotic lung disease.

9. The method of claim 1, wherein the lung disease is emphysema.

10. The method of claim 8, wherein the retinoid is administered in a solution comprising a retinoid, a chlorofluorocarbon solvent, and an amine which is effective to solubilize the retinoid in the chlorofluorocarbon solvent.

11. The method of claim 10, wherein the solution comprises from 0.1 to 10 mg of the retinoid and from 0.1 to 5 mg of the alkylamine per ml of solution.

12. The method of claim 11, wherein the solution comprises from 1 to 2 mg of the retinoid and 0.1 to 0.5 mg of the alkylamine per ml of solution.

13. The method of claim 10, wherein the retinoid is all-trans retinoic acid.

14. The method of claim 10, wherein the alkylamine is a secondary, tertiary or quaternary alkylamine having alkyl groups containing from 2 to 8 carbon atoms.

15. The method of claim 10, wherein the alkylamine is selected from the group consisting of trioctylamine, triethylamine, spermine and tetrabutylammonium bromide.

16. The method of claim 9, wherein the retinoid is administered in a solution comprising a retinoid, a chlorofluorocarbon solvent, and an amine which is effective to solubilize the retinoid in the chlorofluorocarbon solvent.

17. The method of claim 16, wherein the solution comprises from 0.1 to 10 mg of the retinoid and from 0.1 to 5 mg of the alkylamine per ml of solution.

18. The method of claim 17, wherein the solution comprises from 1 to 2 mg of the retinoid and 0.1 to 0.5 mg of the alkylamine per ml of solution.

19. The method of claim 16, wherein the retinoid is all-trans retinoic acid.

20. The method of claim 16, wherein the alkylamine is a secondary, tertiary or quaternary alkylamine having alkyl groups containing from 2 to 8 carbon atoms.

21. The method of claim 16, wherein the alkylamine is selected from the group consisting of trioctylamine, triethylamine, spermine and tetrabutylammonium bromide.

* * * * *